US00PP17594P3

(12) United States Plant Patent
Yomo

(10) Patent No.: US PP17,594 P3
(45) Date of Patent: Apr. 17, 2007

(54) *VERBENA* PLANT NAMED 'SUNMARIVANI'

(50) Latin Name: *Verbena hybrida*
Varietal Denomination: Sunmarivani

(75) Inventor: Yasunori Yomo, Kawasaki (JP)

(73) Assignee: Suntory Flowers Limited, Tokyo (JP)

( * ) Notice: Subject to any disclaimer, the term of this patent is extended or adjusted under 35 U.S.C. 154(b) by 130 days.

(21) Appl. No.: 10/814,623

(22) Filed: Mar. 30, 2004

(65) Prior Publication Data

US 2005/0223457 P1 Oct. 6, 2005

(51) Int. Cl.
*A01H 5/00* (2006.01)

(52) U.S. Cl. ..... Plt./308
(58) Field of Classification Search ..... Plt./308
See application file for complete search history.

(56) References Cited

U.S. PATENT DOCUMENTS

PP10,801 P 2/1999 Nagase

FOREIGN PATENT DOCUMENTS

JP PBR 6630 7/1998
JP PBR 8585 12/2000

OTHER PUBLICATIONS

Flower & Green Catalog 2004, Suntory Flowers, Ltd., (4 pp ), Published 2003, with brief English explanation and partial translation of page 12.
The 2004 Suntory Collection, Jackson & Perkins Wholesale, Inc., (2 pp), Published 2003 with brief English translation.
Pineae Peak Performers featuring the 2004 Suntory Collection, Pinease Greenhoses, Inc., (3 pp), Published 2003 with brief English translation.
Suntory Collection 2004, Moerheim New Plant bv, (5 pp), Published 2003 with brief English translation.
Colour Wave Collection 2003–04, Ramm Botanicals Pty Ltd., (3 pp), Published 2002 with brief English translation.
Explanation of Publications of Japanese PBR Registrations and family documents therein.

*Primary Examiner*—Anne Marie Grunberg
*Assistant Examiner*—Georgia Helmer
(74) *Attorney, Agent, or Firm*—Christie, Parker & Hale, LLP

(57) ABSTRACT

Disclosed herein is a new and distinct variety of *Verbena* plant having a decumbent growth habit. The *Verbena* plant has abundant branching, the whole plant remaining in bloom for a considerable period of time. The flowers are formed in profusion in a spike and the petals display a yellowish white color. The blooming period is from April to November, and the flowering duration is long. The plant exhibits high tolerance to heat and high resistance to rain, pests and disease, particularly powdery mildew.

2 Drawing Sheets

Botanical denomination: *Verbena hybrida.*
Varietal denomination: Sunmarivani.

BACKGROUND OF THE VARIETY

The new variety of *Verbena* plant according to this invention originated as a mutation of *Verbena hybrida* 'Sunmariba'.

The *Verbena* is a very popular plant and is used for flower bedding and potting in the summer season. There are only a few varieties of the *Verbena* plant that have abundant branching, many yellowish white flowers in a spike, and a high resistance to heat, rain, and disease. The new variety, 'Sunmarivani' was discovered as a mutant and has many of those features including a decumbent growth habit, much branching, many flowers in a spike, high tolerance to heat and rain, and resistance to disease and pests.

The new variety *Verbena hybrida* 'Sunmarivani' was discovered as a spontaneous branch mutation of the *Verbena hybrida* 'Sunmariba' (U.S. Plant Pat. No. 10,801) in May 1997 in a field of a nursery at Hakushu-cho, Kitakoma-gun, Yamanashi-ken, Japan.

The mutant *Verbana* plant was propagated by cutting and was grown in pot and bedding from May to November 1997 at Hakushu-cho, Kitakoma-gun, Yamanashi-ken, Japan.

The botanical characteristics of the plant were examined, using similar varieties 'Sunmariba' and 'Sunmaririho' (unpatented). It was concluded that this new *Verbena* variety is distinguishable from other varieties, whose existence is known to us, and is uniform and stable in its characteristics. The new variety of *Verbena* plant was named 'Sunmarivani'.

In the following description, the color-coding is in accordance with The Horticultural Colour Chart of The Royal Horticultural Society, London, England (R.H.S.).

SUMMARY OF THE VARIETY

This new variety is unlike any *Verbena* known to us as evidenced by the following unique combination of characteristics.

1. Decumbent growth habit with abundant branching.
2. Plentiful number of flowers in a spike, having a great profusion of blooms with the entire plant remaining in bloom for a considerable period of time.
3. Long flowering duration.
4. The petal color is yellowish white (near R.H.S. 155B).
5. The plant has a high resistance to rain, heat, disease and pests.

The new variety 'Sunmarivani' differs from the similar variety 'Sunmariba' in the following points.

1. The spreading of plants of 'Sunmarivani' is larger than that of 'Sunmariba'.
2. 'Sunmarivani' does not have anthocyanin pigmentation on stems as is found in 'Sunmariba'.
3. The petal color of 'Sunmarivani' is yellowish white (near R.H.S. 155B), while that of 'Sunmariba' is vivid purple (near R.H.S. N81A).
4. The number of flowers per spike of 'Sunmarivani' is more than that of 'Sunmariba'.

The new variety 'Sunmarivani' differs from the similar variety 'Sunmaririho' in the following points.

1. The stem thickness of 'Sunmarivani' is thicker than that of 'Sunmaririho'.
2. The leaf margin of 'Sunmarivani' is more sharply serrated than that of 'Sunmaririho'.
3. The flower height of 'Sunmarivani' is shorter than that of 'Sunmaririho'.
4. The peduncle length of 'Sunmarivani' is longer than that of 'Sunmaririho'.

This new variety of *Verbena* Plant 'Sunmarivani' was asexually reproduced by the use of cuttings from May to November 1998 at Yokaichi-shi, Shiga-ken, Japan, and homogeneity and stability thereof were confirmed. The instant plant retains its distinctive characteristics and reproduces true to type in successive generations.

BRIEF DESCRIPTION OF THE PHOTOGRAPHS

The depicted plants had been reproduced by the use of cuttings and were photographed during July 2002 while growing outdoors at an age of approximately 6 months at Yokaichi-shi, Shiga-ken, Japan.

DESCRIPTION OF THE VARIETY

Figure 1:
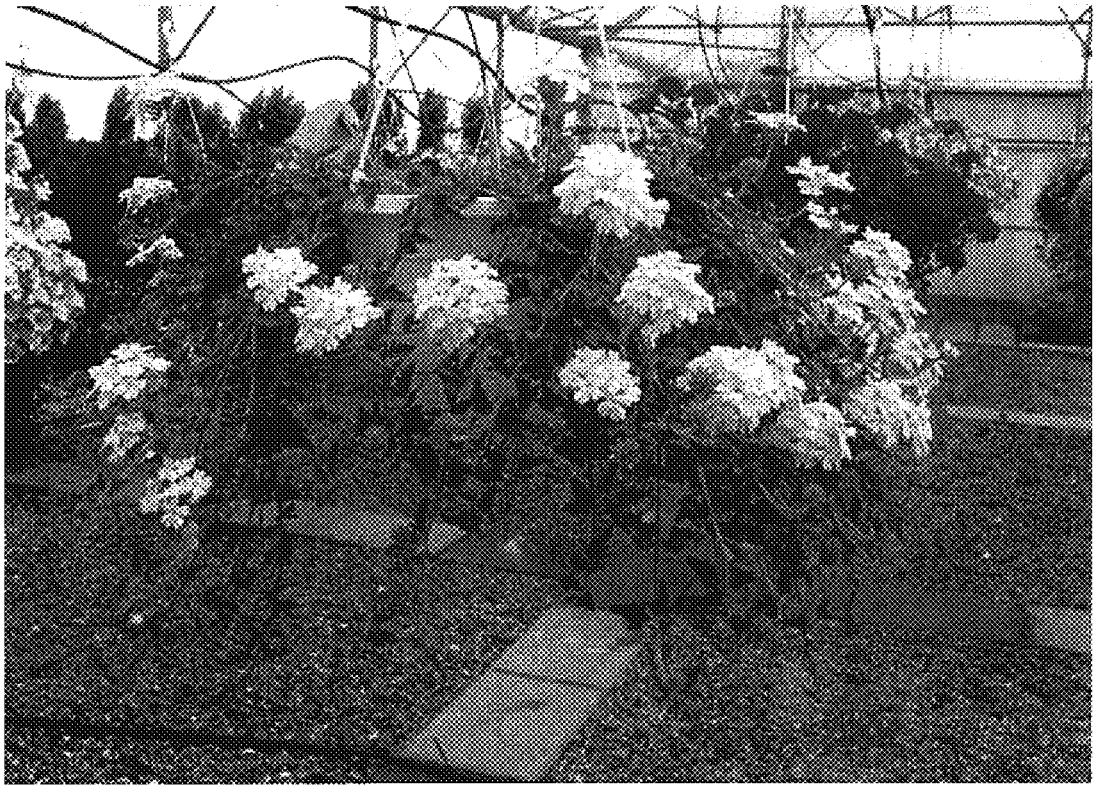
FIG. 1 illustrates a typical plant of the new variety of *Verbena* plant 'Sunmarivani' growing in a hanging pot.
Figure 2:
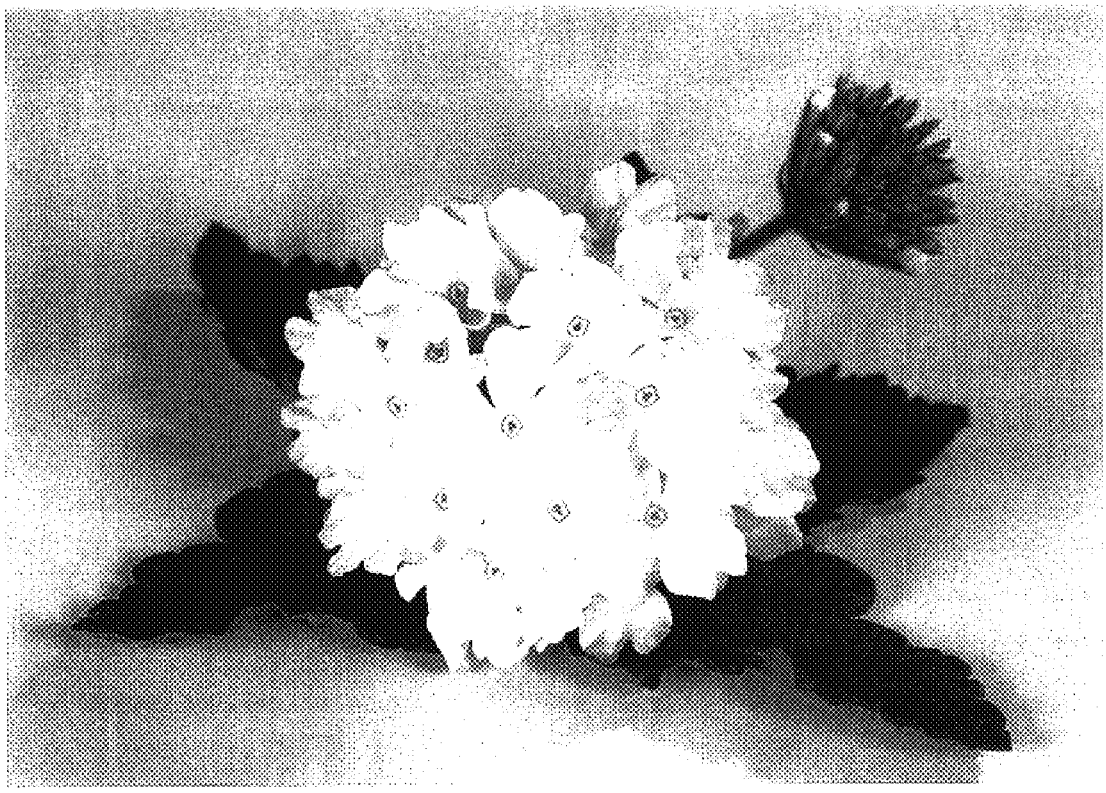
FIG. 2 illustrates a close view of typical foliage and blossoms of the new variety of *Verbena* Plant 'Sunmarivani'.

The botanical characteristics of the new variety of *Verbena* plant named 'Sunmarivani' are as follows.

Plant:
- *Growth habit.*—Decumbent.
- *Plant width.*—Approximately 60–80 cm.
- *Plant height.*—Approximately 10–20 cm.

Stem:
- *Diameter.*—Approximately 3.5–4.0 mm.
- *Anthocyanin pigmentation.*—Absent.
- *Pubescence.*—Moderate.
- *Prickles.*—Absent.
- *Branching.*—Abundant.
- *Subterranean stem.*—Absent.
- *Length of internode.*—Approximately 3.5–4.5 cm.

Leaf:
- *Phyllotaxis.*—Opposite.
- *Shape of blade.*—Hastate.
- *Apex shape.*—Obtuse.
- *Base shape.*—Truncate.
- *Margin.*—Sharply Serrated.
- *Length.*—Approximately 4.0–5.0 cm.
- *Width.*—Approximately 3.0–4.0 cm.
- *Color.*—Upper side: Near R.H.S. 137A (grayish olive green); Lower side: near R.H.S. 144A (strong yellow green).
- *Pubescence.*—Sparse.
- *Petiole.*—Absent.

Flower:
- *Shape of cluster.*—Obconical.
- *Cluster length.*—Approximately 3.5–5.0 cm.
- *Cluster diameter.*—Approximately 5.5–6.5 cm.
- *Facing direction.*—Upward.
- *Floret diameter.*—Approximately 1.5–2.0 cm.
- *Floret length.*—Approximately 1.5–2.0 cm.
- *Color of petal.*—Upper side: near R.H.S. 155B (yellowish white); Lower side: near R.H.S. 156C (yellowish white).
- *Eye color.*—Absent.
- *Variegation.*—Absent.
- *Petal apex.*—Emarginated.
- *Number of petals.*—Generally 5.
- *Calyx length.*—Approximately 1.0–1.5 cm.
- *Calyx shape.*—Tubular. Sepals have an acute apex and are fused at the base.
- *Reproductive organs.*—1 pistil and 4 stamens.
- *Pistil shape.*—Bifid.
- *Anther color.*—Near R.H.S. 1B (yellow green).
- *Filament color.*—Near R.H.S. 1B (yellow green).
- *Pollen.*—Present in a moderate quantity, color near R.H.S. 155B.
- *Stigma color.*—Near R.H.S. 4D (pale yellow green).
- *Style color.*—Near R.H.S. 144B (vivid yellow green).
- *Ovaries.*—Commonly four in number.
- *Peduncle diameter.*—Approximately 1.0–2.0 mm.
- *Peduncle length.*—Approximately 7.0–9.0 cm.
- *Peduncle color.*—Near R.H.S. 137C (Moderate yellow green).
- *Number of flowers per spike.*—Approximately 17.
- *Flowering period.*—April to November in the southern Kanto area, Japan. The plant shape does not change throughout this period. A typical flower commonly lasts 5 to 7 days on the plant when experiencing a temperature of approximately 20° C.
- *Fruit and seed.*—Fruit and seed production has not been observed.

Physiological and ecological characteristics:
- *Winter hardiness.*—USDA Hardiness Zone 4–9 (Grown as perennial).
- *Heat tolerance.*—The plant grows well at temperature up to at least 35° C.
- *Disease and pest resistance.*—Resistant to powdery mildew. No serious damage by pathogen and pests common to *Verbena* has been observed.

It is claimed:

1. A new and distinct variety of *Verbena* plant named 'Sunmarivani', substantially as herein illustrated and described.

* * * * *